(12) United States Patent
Gilland

(10) Patent No.: US 8,452,366 B2
(45) Date of Patent: May 28, 2013

(54) MEDICAL MONITORING DEVICE WITH FLEXIBLE CIRCUITRY

(75) Inventor: Bruce Gilland, Superior, CO (US)

(73) Assignee: Covidien LP, Mansfield, MA (US)

( * ) Notice: Subject to any disclaimer, the term of this patent is extended or adjusted under 35 U.S.C. 154(b) by 897 days.

(21) Appl. No.: 12/404,887

(22) Filed: Mar. 16, 2009

(65) Prior Publication Data

US 2010/0234706 A1 Sep. 16, 2010

(51) Int. Cl.
*A61B 5/1455* (2006.01)

(52) U.S. Cl.
USPC .......................................... 600/344; 600/310

(58) Field of Classification Search
USPC ................................. 600/309–344
See application file for complete search history.

(56) References Cited

U.S. PATENT DOCUMENTS

| | | | |
|---|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

International Search Report PCT/US2010/025360, 4 pages, mailed May 7, 2010.

(Continued)

*Primary Examiner* — Eric Winakur
*Assistant Examiner* — Marjan Fardanesh
(74) *Attorney, Agent, or Firm* — Fletcher Yoder

(57) ABSTRACT

Embodiments described herein may include systems and methods for monitoring physiological parameters of a patient. Specifically, embodiments disclose the use of a flexible circuitry in a medical sensor that is small and lightweight and easily bendable, such that it may be comfortably affixed to a patient while also providing added electronic functions, such as digital conversion and wireless capability.

20 Claims, 6 Drawing Sheets

U.S. PATENT DOCUMENTS

| | | | |
|---|---|---|---|
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp, Jr. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |

| | | | | | | |
|---|---|---|---|---|---|---|
| 5,474,065 | A | 12/1995 | Meathrel et al. | 5,752,914 | A | 5/1998 | DeLonzor et al. |
| 5,482,034 | A | 1/1996 | Lewis et al. | 5,755,226 | A | 5/1998 | Carim et al. |
| 5,482,036 | A | 1/1996 | Diab et al. | 5,758,644 | A | 6/1998 | Diab et al. |
| 5,483,646 | A | 1/1996 | Uchikoga | 5,760,910 | A | 6/1998 | Lepper, Jr. et al. |
| 5,485,847 | A | 1/1996 | Baker, Jr. | 5,766,125 | A | 6/1998 | Aoyagi et al. |
| 5,490,505 | A | 2/1996 | Diab et al. | 5,766,127 | A | 6/1998 | Pologe et al. |
| 5,490,523 | A | 2/1996 | Isaacson et al. | 5,769,785 | A | 6/1998 | Diab et al. |
| 5,491,299 | A | 2/1996 | Naylor et al. | 5,772,587 | A | 6/1998 | Gratton et al. |
| 5,494,032 | A | 2/1996 | Robinson et al. | 5,774,213 | A | 6/1998 | Trebino et al. |
| 5,497,771 | A | 3/1996 | Rosenheimer | 5,776,058 | A | 7/1998 | Levinson et al. |
| 5,499,627 | A | 3/1996 | Steuer et al. | 5,776,059 | A | 7/1998 | Kaestle et al. |
| 5,503,148 | A | 4/1996 | Pologe et al. | 5,779,630 | A | 7/1998 | Fein et al. |
| 5,505,199 | A | 4/1996 | Kim | 5,779,631 | A | 7/1998 | Chance |
| 5,507,286 | A | 4/1996 | Solenberger | 5,782,237 | A | 7/1998 | Casciani et al. |
| 5,511,546 | A | 4/1996 | Hon | 5,782,756 | A | 7/1998 | Mannheimer |
| 5,517,988 | A | 5/1996 | Gerhard | 5,782,757 | A | 7/1998 | Diab et al. |
| 5,520,177 | A | 5/1996 | Ogawa et al. | 5,782,758 | A | 7/1998 | Ausec et al. |
| 5,521,851 | A | 5/1996 | Wei et al. | 5,786,592 | A | 7/1998 | Hök |
| 5,522,388 | A | 6/1996 | Ishikawa et al. | 5,790,729 | A | 8/1998 | Pologe et al. |
| 5,524,617 | A | 6/1996 | Mannheimer | 5,792,052 | A | 8/1998 | Isaacson et al. |
| 5,529,064 | A | 6/1996 | Rall et al. | 5,795,292 | A | 8/1998 | Lewis et al. |
| 5,533,507 | A | 7/1996 | Potratz et al. | 5,797,841 | A | 8/1998 | DeLonzor et al. |
| 5,551,423 | A | 9/1996 | Sugiura | 5,800,348 | A | 9/1998 | Kaestle |
| 5,551,424 | A | 9/1996 | Morrison et al. | 5,800,349 | A | 9/1998 | Isaacson et al. |
| 5,553,614 | A | 9/1996 | Chance | 5,803,910 | A | 9/1998 | Potratz |
| 5,553,615 | A | 9/1996 | Carim et al. | 5,807,246 | A | 9/1998 | Sakaguchi et al. |
| 5,555,882 | A | 9/1996 | Richardson et al. | 5,807,247 | A | 9/1998 | Merchant et al. |
| 5,558,096 | A | 9/1996 | Palatnik | 5,807,248 | A | 9/1998 | Mills |
| 5,560,355 | A | 10/1996 | Merchant et al. | 5,810,723 | A | 9/1998 | Aldrich |
| 5,564,417 | A | 10/1996 | Chance | 5,810,724 | A | 9/1998 | Gronvall |
| 5,575,284 | A | 11/1996 | Athan et al. | 5,813,980 | A | 9/1998 | Levinson et al. |
| 5,575,285 | A | 11/1996 | Takanashi et al. | 5,817,008 | A | 10/1998 | Rafert et al. |
| 5,577,500 | A | 11/1996 | Potratz | 5,817,009 | A | 10/1998 | Rosenheimer et al. |
| 5,582,169 | A | 12/1996 | Oda et al. | 5,817,010 | A | 10/1998 | Hibl |
| 5,584,296 | A | 12/1996 | Cui et al. | 5,818,985 | A | 10/1998 | Merchant et al. |
| 5,588,425 | A | 12/1996 | Sackner et al. | 5,820,550 | A | 10/1998 | Polson et al. |
| 5,588,427 | A | 12/1996 | Tien | 5,823,950 | A | 10/1998 | Diab et al. |
| 5,590,652 | A | 1/1997 | Inai | 5,823,952 | A | 10/1998 | Levinson et al. |
| 5,595,176 | A | 1/1997 | Yamaura | 5,827,182 | A | 10/1998 | Raley et al. |
| 5,596,986 | A | 1/1997 | Goldfarb | 5,830,135 | A | 11/1998 | Bosque et al. |
| 5,611,337 | A | 3/1997 | Bukta | 5,830,136 | A | 11/1998 | DeLonzor et al. |
| 5,617,852 | A | 4/1997 | MacGregor | 5,830,137 | A | 11/1998 | Scharf |
| 5,619,992 | A | 4/1997 | Guthrie et al. | 5,839,439 | A | 11/1998 | Nierlich et al. |
| 5,626,140 | A | 5/1997 | Feldman et al. | RE36,000 | E | 12/1998 | Swedlow et al. |
| 5,630,413 | A | 5/1997 | Thomas et al. | 5,842,979 | A | 12/1998 | Jarman et al. |
| 5,632,272 | A | 5/1997 | Diab et al. | 5,842,981 | A | 12/1998 | Larsen et al. |
| 5,632,273 | A | 5/1997 | Suzuki | 5,842,982 | A | 12/1998 | Mannheimer |
| 5,634,459 | A | 6/1997 | Gardosi | 5,846,190 | A | 12/1998 | Woehrle |
| 5,638,593 | A | 6/1997 | Gerhardt et al. | 5,851,178 | A | 12/1998 | Aronow |
| 5,638,818 | A | 6/1997 | Diab et al. | 5,851,179 | A | 12/1998 | Ritson et al. |
| 5,645,060 | A | 7/1997 | Yorkey et al. | 5,853,364 | A | 12/1998 | Baker, Jr. et al. |
| 5,645,440 | A | 7/1997 | Tobler et al. | 5,860,919 | A | 1/1999 | Kiani-Azarbayjany et al. |
| 5,660,567 | A | 8/1997 | Nierlich et al. | 5,865,736 | A | 2/1999 | Baker, Jr. et al. |
| 5,662,105 | A | 9/1997 | Tien | 5,871,442 | A | 2/1999 | Madarasz et al. |
| 5,662,106 | A | 9/1997 | Swedlow et al. | 5,879,294 | A | 3/1999 | Anderson et al. |
| 5,666,952 | A | 9/1997 | Fuse et al. | 5,885,213 | A | 3/1999 | Richardson et al. |
| 5,671,529 | A | 9/1997 | Nelson | 5,890,929 | A | 4/1999 | Mills et al. |
| 5,673,692 | A | 10/1997 | Schulze et al. | 5,891,021 | A | 4/1999 | Dillon et al. |
| 5,673,693 | A | 10/1997 | Solenberger | 5,891,022 | A | 4/1999 | Pologe |
| 5,676,139 | A | 10/1997 | Goldberger et al. | 5,891,024 | A | 4/1999 | Jarman et al. |
| 5,676,141 | A | 10/1997 | Hollub | 5,891,025 | A | 4/1999 | Buschmann et al. |
| 5,678,544 | A | 10/1997 | DeLonzor et al. | 5,891,026 | A | 4/1999 | Wang et al. |
| 5,680,857 | A | 10/1997 | Pelikan et al. | 5,902,235 | A | 5/1999 | Lewis et al. |
| 5,685,299 | A | 11/1997 | Diab et al. | 5,910,108 | A | 6/1999 | Solenberger |
| 5,685,301 | A | 11/1997 | Klomhaus | 5,911,690 | A | 6/1999 | Rall |
| 5,687,719 | A | 11/1997 | Sato et al. | 5,912,656 | A | 6/1999 | Tham et al. |
| 5,687,722 | A | 11/1997 | Tien et al. | 5,913,819 | A | 6/1999 | Taylor et al. |
| 5,692,503 | A | 12/1997 | Kuenstner | 5,916,154 | A | 6/1999 | Hobbs et al. |
| 5,692,505 | A | 12/1997 | Fouts | 5,916,155 | A | 6/1999 | Levinson et al. |
| 5,709,205 | A | 1/1998 | Bukta | 5,919,133 | A | 7/1999 | Taylor et al. |
| 5,713,355 | A | 2/1998 | Richardson et al. | 5,919,134 | A | 7/1999 | Diab |
| 5,724,967 | A | 3/1998 | Venkatachalam | 5,920,263 | A | 7/1999 | Huttenhoff et al. |
| 5,727,547 | A | 3/1998 | Levinson et al. | 5,921,921 | A | 7/1999 | Potratz et al. |
| 5,731,582 | A | 3/1998 | West | 5,922,607 | A | 7/1999 | Bernreuter |
| D393,830 | S | 4/1998 | Tobler et al. | 5,924,979 | A | 7/1999 | Swedlow et al. |
| 5,743,260 | A | 4/1998 | Chung et al. | 5,924,980 | A | 7/1999 | Coetzee |
| 5,743,263 | A | 4/1998 | Baker, Jr. | 5,924,982 | A | 7/1999 | Chin |
| 5,746,206 | A | 5/1998 | Mannheimer | 5,924,985 | A | 7/1999 | Jones |
| 5,746,697 | A | 5/1998 | Swedlow et al. | 5,934,277 | A | 8/1999 | Mortz |

| | | | | | | |
|---|---|---|---|---|---|---|
| 5,934,925 | A | 8/1999 | Tobler et al. | 6,213,952 B1 | 4/2001 | Finarov et al. |
| 5,940,182 | A | 8/1999 | Lepper, Jr. et al. | 6,217,523 B1 | 4/2001 | Amano et al. |
| 5,954,644 | A | 9/1999 | Dettling et al. | 6,222,189 B1 | 4/2001 | Misner et al. |
| 5,960,610 | A | 10/1999 | Levinson et al. | 6,226,539 B1 | 5/2001 | Potratz |
| 5,961,450 | A | 10/1999 | Merchant et al. | 6,226,540 B1 | 5/2001 | Bernreuter |
| 5,961,452 | A | 10/1999 | Chung et al. | 6,229,856 B1 | 5/2001 | Diab et al. |
| 5,964,701 | A | 10/1999 | Asada et al. | 6,230,035 B1 | 5/2001 | Aoyagi et al. |
| 5,971,930 | A | 10/1999 | Elghazzawi | 6,233,470 B1 | 5/2001 | Tsuchiya |
| 5,978,691 | A | 11/1999 | Mills | 6,236,871 B1 | 5/2001 | Tsuchiya |
| 5,978,693 | A | 11/1999 | Hamilton et al. | 6,236,872 B1 | 5/2001 | Diab et al. |
| 5,983,122 | A | 11/1999 | Jarman et al. | 6,240,305 B1 | 5/2001 | Tsuchiya |
| 5,987,343 | A | 11/1999 | Kinast | 6,253,097 B1 | 6/2001 | Aronow et al. |
| 5,991,648 | A | 11/1999 | Levin | 6,253,098 B1 | 6/2001 | Walker et al. |
| 5,995,855 | A | 11/1999 | Kiani et al. | 6,256,523 B1 | 7/2001 | Diab et al. |
| 5,995,856 | A | 11/1999 | Mannheimer et al. | 6,256,524 B1 | 7/2001 | Walker et al. |
| 5,995,858 | A | 11/1999 | Kinast | 6,261,236 B1 | 7/2001 | Grimblatov |
| 5,995,859 | A | 11/1999 | Takahashi | 6,263,221 B1 | 7/2001 | Chance et al. |
| 5,997,343 | A | 12/1999 | Mills et al. | 6,263,222 B1 | 7/2001 | Diab et al. |
| 5,999,834 | A | 12/1999 | Wang et al. | 6,263,223 B1 | 7/2001 | Shepherd et al. |
| 6,002,952 | A | 12/1999 | Diab et al. | 6,266,546 B1 | 7/2001 | Steuer et al. |
| 6,005,658 | A | 12/1999 | Kaluza et al. | 6,266,547 B1 | 7/2001 | Walker et al. |
| 6,006,120 | A | 12/1999 | Levin | 6,272,363 B1 | 8/2001 | Casciani et al. |
| 6,011,985 | A | 1/2000 | Athan et al. | 6,278,522 B1 | 8/2001 | Lepper, Jr. et al. |
| 6,011,986 | A | 1/2000 | Diab et al. | 6,280,213 B1 | 8/2001 | Tobler et al. |
| 6,014,576 | A | 1/2000 | Raley | 6,280,381 B1 | 8/2001 | Malin et al. |
| 6,018,673 | A | 1/2000 | Chin et al. | 6,285,894 B1 | 9/2001 | Oppelt et al. |
| 6,018,674 | A | 1/2000 | Aronow | 6,285,895 B1 | 9/2001 | Ristolainen et al. |
| 6,022,321 | A | 2/2000 | Amano et al. | 6,285,896 B1 | 9/2001 | Tobler et al. |
| 6,023,541 | A | 2/2000 | Merchant et al. | 6,298,252 B1 | 10/2001 | Kovach et al. |
| 6,026,312 | A | 2/2000 | Shemwell et al. | 6,308,089 B1 | 10/2001 | Von der Ruhr et al. |
| 6,026,314 | A | 2/2000 | Amerov et al. | 6,321,100 B1 | 11/2001 | Parker |
| 6,031,603 | A | 2/2000 | Fine et al. | 6,330,468 B1 | 12/2001 | Scharf |
| 6,035,223 | A | 3/2000 | Baker, Jr. | 6,334,065 B1 | 12/2001 | Al-Ali et al. |
| 6,036,642 | A | 3/2000 | Diab et al. | 6,339,715 B1 | 1/2002 | Bahr et al. |
| 6,041,247 | A | 3/2000 | Weckstrom et al. | 6,343,223 B1 | 1/2002 | Chin et al. |
| 6,044,283 | A | 3/2000 | Fein et al. | 6,343,224 B1 | 1/2002 | Parker |
| 6,047,201 | A | 4/2000 | Jackson, III | 6,349,228 B1 | 2/2002 | Kiani et al. |
| 6,061,584 | A | 5/2000 | Lovejoy et al. | 6,351,658 B1 | 2/2002 | Middleman et al. |
| 6,064,898 | A | 5/2000 | Aldrich | 6,353,750 B1 | 3/2002 | Kimura et al. |
| 6,064,899 | A | 5/2000 | Fein et al. | 6,356,774 B1 | 3/2002 | Bernstein et al. |
| 6,067,462 | A | 5/2000 | Diab et al. | 6,360,113 B1 | 3/2002 | Dettling |
| 6,073,038 | A | 6/2000 | Wang et al. | 6,360,114 B1 | 3/2002 | Diab et al. |
| 6,078,833 | A | 6/2000 | Hueber | 6,361,501 B1 | 3/2002 | Amano et al. |
| 6,081,735 | A | 6/2000 | Diab et al. | 6,363,269 B1 | 3/2002 | Hanna et al. |
| 6,081,742 | A | 6/2000 | Amano et al. | 6,370,408 B1 | 4/2002 | Merchant et al. |
| 6,083,157 | A | 7/2000 | Noller | 6,370,409 B1 | 4/2002 | Chung et al. |
| 6,083,172 | A | 7/2000 | Baker, Jr. et al. | 6,374,129 B1 | 4/2002 | Chin et al. |
| 6,088,607 | A | 7/2000 | Diab et al. | 6,377,829 B1 | 4/2002 | Al-Ali |
| 6,094,592 | A | 7/2000 | Yorkey et al. | 6,381,479 B1 | 4/2002 | Norris |
| 6,095,974 | A | 8/2000 | Shemwell et al. | 6,381,480 B1 | 4/2002 | Stoddart et al. |
| 6,104,938 | A | 8/2000 | Huiku et al. | 6,385,471 B1 | 5/2002 | Mortz |
| 6,112,107 | A | 8/2000 | Hannula | 6,385,821 B1 | 5/2002 | Modgil et al. |
| 6,113,541 | A | 9/2000 | Dias et al. | 6,388,240 B2 | 5/2002 | Schulz et al. |
| 6,115,621 | A | 9/2000 | Chin | 6,393,310 B1 | 5/2002 | Kuenstner |
| 6,122,535 | A | 9/2000 | Kaestle et al. | 6,397,091 B2 | 5/2002 | Diab et al. |
| 6,133,994 | A | 10/2000 | Mathews et al. | 6,397,092 B1 | 5/2002 | Norris et al. |
| 6,135,952 | A | 10/2000 | Coetzee | 6,397,093 B1 | 5/2002 | Aldrich |
| 6,144,444 | A | 11/2000 | Haworth et al. | 6,400,971 B1 | 6/2002 | Finarov et al. |
| 6,144,867 | A | 11/2000 | Walker et al. | 6,400,972 B1 | 6/2002 | Fine |
| 6,144,868 | A | 11/2000 | Parker | 6,402,690 B1 | 6/2002 | Rhee et al. |
| 6,149,481 | A | 11/2000 | Wang et al. | 6,408,198 B1 | 6/2002 | Hanna et al. |
| 6,150,951 | A | 11/2000 | Olejniczak | 6,411,832 B1 | 6/2002 | Guthermann |
| 6,151,107 | A | 11/2000 | Schöllermann et al. | 6,411,833 B1 | 6/2002 | Baker, Jr. et al. |
| 6,151,518 | A | 11/2000 | Hayashi | 6,419,671 B1 | 7/2002 | Lemberg |
| 6,152,754 | A | 11/2000 | Gerhardt et al. | 6,421,549 B1 | 7/2002 | Jacques |
| 6,154,667 | A | 11/2000 | Miura et al. | 6,430,423 B2 | 8/2002 | DeLonzor et al. |
| 6,157,850 | A | 12/2000 | Diab et al. | 6,430,513 B1 | 8/2002 | Wang et al. |
| 6,163,715 | A | 12/2000 | Larsen et al. | 6,430,525 B1 | 8/2002 | Weber et al. |
| 6,165,005 | A | 12/2000 | Mills et al. | 6,434,408 B1 | 8/2002 | Heckel |
| 6,173,196 B1 | | 1/2001 | Delonzor et al. | 6,438,399 B1 | 8/2002 | Kurth |
| 6,178,343 B1 | | 1/2001 | Bindszus et al. | 6,449,501 B1 | 9/2002 | Reuss |
| 6,181,958 B1 | | 1/2001 | Steuer et al. | 6,453,183 B1 | 9/2002 | Walker |
| 6,181,959 B1 | | 1/2001 | Schöllermann et al. | 6,453,184 B1 | 9/2002 | Hyogo et al. |
| 6,184,521 B1 | | 2/2001 | Coffin, IV et al. | 6,456,862 B2 | 9/2002 | Benni |
| 6,188,470 B1 | | 2/2001 | Grace | 6,461,305 B1 | 10/2002 | Schnall |
| 6,192,260 B1 | | 2/2001 | Chance | 6,463,310 B1 | 10/2002 | Swedlow et al. |
| 6,195,575 B1 | | 2/2001 | Levinson | 6,463,311 B1 | 10/2002 | Diab |
| 6,198,951 B1 | | 3/2001 | Kosuda et al. | 6,466,808 B1 | 10/2002 | Chin et al. |
| 6,206,830 B1 | | 3/2001 | Diab et al. | 6,466,809 B1 | 10/2002 | Riley |

| Patent | Date | Inventor |
|---|---|---|
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |

| Patent Number | Date | Inventor |
|---|---|---|
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boas et al. |
| 7,047,056 B2 | 5/2006 | Hannula et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom et al. |
| 7,187,960 B2 * | 3/2007 | Abreu .................. 600/310 |
| 7,190,987 B2 | 3/2007 | Lindekugel et al. |
| 7,198,778 B2 | 4/2007 | Achilefu et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0144596 A1 * | 7/2003 | Tsubata .................. 600/500 |
| 2003/0149349 A1 * | 8/2003 | Jensen .................. 600/372 |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |

| | | | |
|---|---|---|---|
| 2004/0204637 A1 | 10/2004 | Diab et al. | |
| 2004/0204638 A1 | 10/2004 | Diab et al. | |
| 2004/0204639 A1 | 10/2004 | Casciani et al. | |
| 2004/0204865 A1 | 10/2004 | Lee et al. | |
| 2004/0210146 A1 | 10/2004 | Diab et al. | |
| 2004/0214365 A1* | 10/2004 | Joshi | 438/48 |
| 2004/0215069 A1 | 10/2004 | Mannheimer | |
| 2004/0230107 A1 | 11/2004 | Asada et al. | |
| 2004/0230108 A1 | 11/2004 | Melker et al. | |
| 2004/0236196 A1 | 11/2004 | Diab et al. | |
| 2004/0242980 A1 | 12/2004 | Kiani et al. | |
| 2004/0249252 A1 | 12/2004 | Fine et al. | |
| 2004/0257557 A1 | 12/2004 | Block | |
| 2004/0260161 A1 | 12/2004 | Melker et al. | |
| 2004/0267103 A1 | 12/2004 | Li et al. | |
| 2004/0267104 A1 | 12/2004 | Hannula et al. | |
| 2004/0267140 A1 | 12/2004 | Ito et al. | |
| 2005/0004479 A1 | 1/2005 | Townsend et al. | |
| 2005/0010092 A1 | 1/2005 | Weber et al. | |
| 2005/0020887 A1 | 1/2005 | Goldberg | |
| 2005/0020894 A1 | 1/2005 | Norris et al. | |
| 2005/0033128 A1 | 2/2005 | Ali et al. | |
| 2005/0033129 A1 | 2/2005 | Edgar, Jr. et al. | |
| 2005/0043599 A1 | 2/2005 | O'Mara | |
| 2005/0043600 A1 | 2/2005 | Diab et al. | |
| 2005/0049470 A1 | 3/2005 | Terry | |
| 2005/0049471 A1 | 3/2005 | Aceti | |
| 2005/0075550 A1 | 4/2005 | Lindekugel | |
| 2005/0113651 A1 | 5/2005 | Wood et al. | |
| 2005/0177034 A1 | 8/2005 | Beaumont | |
| 2005/0197548 A1 | 9/2005 | Dietiker | |
| 2005/0228248 A1 | 10/2005 | Dietiker | |
| 2005/0228298 A1 | 10/2005 | Banet | |
| 2005/0277819 A1 | 12/2005 | Kiani et al. | |
| 2005/0283059 A1 | 12/2005 | Iyer et al. | |
| 2006/0058594 A1 | 3/2006 | Ishizuka et al. | |
| 2006/0084852 A1 | 4/2006 | Mason et al. | |
| 2006/0089547 A1 | 4/2006 | Sarussi | |
| 2006/0106294 A1 | 5/2006 | Maser et al. | |
| 2006/0195028 A1 | 8/2006 | Hannula et al. | |
| 2006/0224058 A1 | 10/2006 | Mannheimer | |
| 2006/0229509 A1* | 10/2006 | Al-Ali et al. | 600/310 |
| 2006/0247501 A1 | 11/2006 | Ali | |
| 2006/0258921 A1 | 11/2006 | Addison et al. | |
| 2006/0276700 A1 | 12/2006 | O'Neil | |
| 2006/0282001 A1 | 12/2006 | Noel | |
| 2007/0032710 A1 | 2/2007 | Raridan et al. | |
| 2007/0032712 A1 | 2/2007 | Raridan et al. | |
| 2007/0032715 A1 | 2/2007 | Eghbal et al. | |
| 2007/0073121 A1 | 3/2007 | Hoarau et al. | |
| 2007/0073125 A1 | 3/2007 | Hoarau et al. | |
| 2007/0073126 A1 | 3/2007 | Raridan, Jr. | |
| 2007/0073128 A1 | 3/2007 | Hoarau et al. | |
| 2007/0123756 A1* | 5/2007 | Kitajima et al. | 600/300 |
| 2007/0129613 A1* | 6/2007 | Rochester et al. | 600/310 |
| 2008/0177163 A1 | 7/2008 | Wang | |
| 2008/0312517 A1 | 12/2008 | Genoe | |
| 2009/0012380 A1 | 1/2009 | Gonopolskiy | |
| 2009/0167205 A1 | 7/2009 | Peterson | |
| 2009/0240125 A1* | 9/2009 | Such et al. | 600/323 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| EP | 0724860 | 8/1996 |
| FR | 2685865 | 7/1993 |
| JP | 2111343 | 4/1990 |
| JP | 3116259 | 12/1991 |
| JP | 3116260 | 12/1991 |
| JP | 5049625 | 3/1993 |
| JP | 6014906 | 1/1994 |
| JP | 6269430 | 9/1994 |
| JP | 7001273 | 1/1995 |
| JP | 7236625 | 9/1995 |
| JP | 2000237170 | 9/2000 |
| JP | 2003275192 | 9/2003 |
| JP | 2004089546 | 3/2004 |
| JP | 2004159810 | 6/2004 |
| JP | 2004329406 | 11/2004 |
| JP | 2004337605 | 12/2004 |
| JP | 2004344367 | 12/2004 |
| JP | 2004351107 | 12/2004 |
| JP | 26075354 A2 | 3/2006 |
| JP | 26325766 A2 | 12/2006 |
| JP | 27117641 A2 | 5/2007 |
| JP | 27190122 A2 | 8/2007 |
| JP | 27330708 A2 | 12/2007 |
| WO | WO8909566 | 10/1989 |
| WO | WO9001293 | 2/1990 |
| WO | WO9111137 | 8/1991 |
| WO | WO9502358 | 1/1995 |
| WO | WO9736536 | 10/1997 |
| WO | WO9857577 | 12/1998 |
| WO | WO9947039 | 9/1999 |
| WO | WO0059374 | 10/2000 |
| WO | WO2005010567 | 2/2005 |
| WO | WO2005010568 | 2/2005 |
| WO | WO2007041296 A1 | 4/2007 |
| WO | WO2007097754 A1 | 8/2007 |
| WO | WO 2009/124076 A1 | 10/2009 |

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

http://www.fcw.com.my/fujifilm.html.

John Boyd.; "Epson Takes Major Step Toward Flexible Electronics," Technology Newsline, http://www.epson.co.jp/e/newsroom/feature_tech.htm (May 2005).

John Boyd.; "Epson Succeeds in Printing Transistors with Liquid Silicon," Technology Newsline, http://w3.epson.com.tw/epson/images/news/20060806%5CVol605En.pdf (May 2006).

* cited by examiner

MEDICAL MONITORING DEVICE WITH FLEXIBLE CIRCUITRY

BACKGROUND

The present disclosure relates generally to medical devices and, more particularly, to medical monitoring devices.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The sensor is usually small, lightweight, and flexible so that it may be easily and comfortably held against the patient's tissue. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

Due to the flexibility and small size of the pulse oximeter sensor, the amount of circuitry included in the sensor is usually rather limited. Accordingly, the sensor is usually coupled through a cable to a monitor that sends and receives electrical signals to the sensor and includes circuitry used for processing the received signals and performing other functions that are outside the limited capabilities of the sensor.

This conventional configuration, however, may have several disadvantages. For example, the cable may tend to pick up unwanted electrical noise, thereby reducing the signal-to-noise ratio of transmitted signal. For another example, the transmission of analog signals through the resistive cable may result in substantial power loss. For yet another example, the patient's comfort and mobility may be limited by the cable running between the sensor and the monitor. It may be desirable, therefore, to provide a medical sensor with improved processing functionality while maintaining the sensor's flexibility and comfort.

BRIEF DESCRIPTION OF THE DRAWINGS

Advantages of the disclosure may become apparent upon reading the following detailed description and upon reference to the drawings in which.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is directed to an improved medical sensor that includes flexible circuitry. For the purposes of the present specification, the term "flexible circuit" is intended to describe a deformable integrated circuit that may be flexed without damaging the circuit. By including flexible circuitry within the sensor, the processing capabilities of the sensor may be improved while maintaining the sensor's flexibility and comfort. The enhanced processing capabilities of the sensor may include amplification and filtering of signals received by the sensing components of the sensor and analog-to-digital conversion of the received signals. The digital signals may then be transmitted to the monitor with less power consumption and higher signal-to-noise ratio. Certain other embodiments may additionally include circuitry that enables the sensor to wirelessly transmit the digital signals to the monitor, thereby eliminating the communications cable. Further embodiments may include a sensor with circuitry that enables the sensor to calculate and/or display some physiological parameters.

Figure 1:
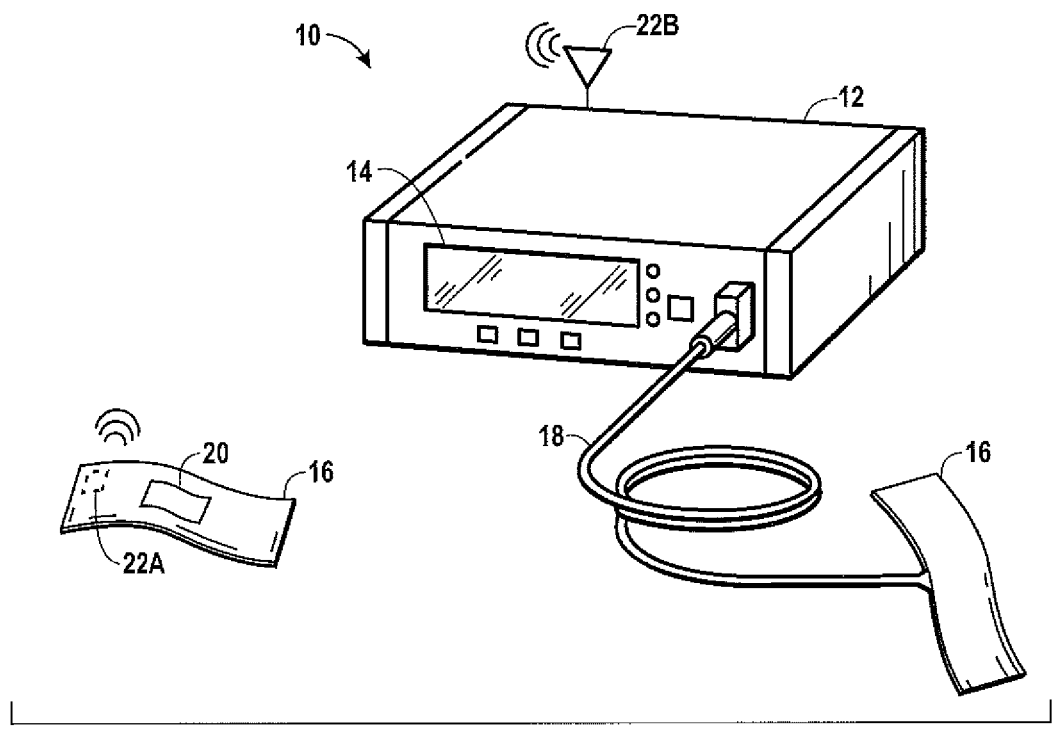
FIG. 1 is a perspective view of a medical monitoring system with flexible, bandage-style sensors in accordance with an embodiment.

Referring to the figures and turning initially to FIG. 1, a medical monitoring device is illustrated in accordance with an embodiment and is generally designated by the reference numeral 10. The device 10 may include a monitor 12 which may house hardware and software configured to compute various physiological parameters. The monitor 12 may be configured to operate as a pulse oximeter or as a multi-parameter monitor, such as those available from Nellcor Puritan Bennett L.L.C. and/or Covidien. The monitor 12 may include a display 14 to display the various physiological parameters.

For example, the display 14 may display the pulse rate and the concentration of a blood analyte, such as, percent oxygen saturation of hemoglobin, for example. The display 14 may show the physiological parameters and calculated values in any appropriate manner. For example, the calculated values may be displayed numerically and/or as a waveform over time. Additionally, any notifications or alerts prompted by abnormal measurements, calculated values and/or other conditions may be displayed.

One or more flexible sensors 16, in accordance with various embodiments, may be communicatively coupled to the monitor 12. As shown in FIG. 1, the sensors 16 are flexible and, thus, may be attached to the tissue of a patient in a variety of ways. For example, the sensor 16 may be wrapped around a portion of a patient, such as a finger, toe, arm, leg, earlobe, etc. In other embodiments, the sensor may be held against the patients' forehead or torso, such that the sensor fits the contours of the tissue.

In some embodiments, the sensor 16 may be communicatively coupled to the monitor 12 via a cable 18. In other embodiments, however, the sensor 16 may communicate with the monitor 12 wirelessly. In the latter case, both the monitor 12 and the sensor 16 may include wireless devices that allow the monitor and the sensor to communicate as will be explained below in reference to FIG. 6. By eliminating the cable 18, the patient is no longer tethered to the monitor 12 and may move more freely without the risk of inadvertently jerking or damaging the cable 18. In this way, the sensor 16 may be less susceptible to movement or accidental removal, and the risk of the sensor 16 or the monitor 12 is reduced.

The sensor 16 may also include a display 20 that provides information regarding the physiological parameters of the patient, such as blood oxygenation and heart rate. In some embodiments, the sensor 16 may receive the displayed physiological parameters from the monitor 12. As such, the sensor 16 may transmit the raw physiological data to the monitor 12, and the monitor 12 may then calculate physiological parameters based the physiological data and transmit the physiological parameters back to the sensor 16 for display. In other embodiments, the sensor 16 may include flexible circuitry configured to calculate the physiological parameters based on the data gathered by the sensor 16. In this way, the sensor 16 may be a stand-alone unit, capable of providing physiological data without the use of the monitor 12. The sensor 16 may, therefore, be used in situations in which a monitor 12 may not be readily available or convenient, such as during an emergency, patient transportation, or other situations where the patient is away from a medical facility. By displaying physiological parameters directly on the sensor 16, a medical service provider may devote greater attention to the patient while obtaining important information regarding the patient's health.

Figure 2:
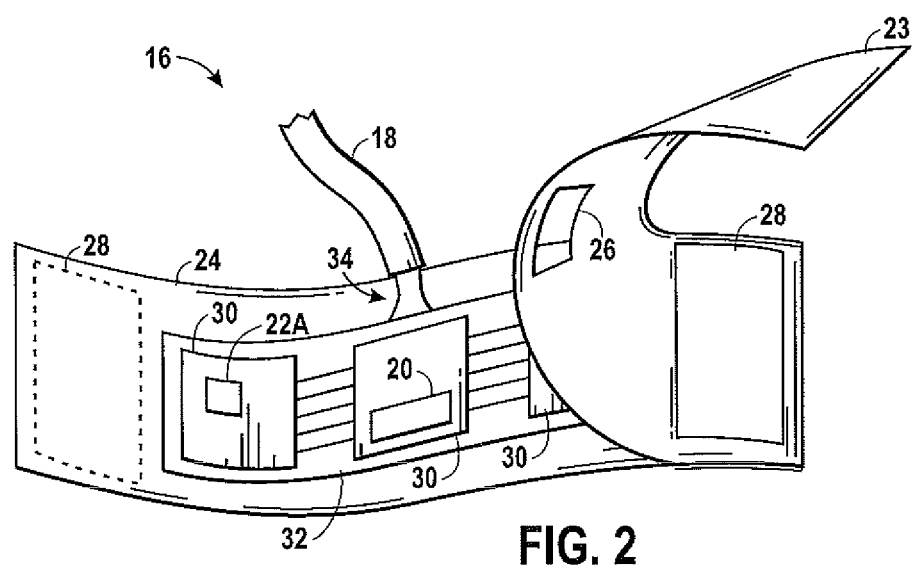
FIG. 2 is a perspective view of a partially assembled flexible, bandage-style sensor in accordance with an embodiment in which the sensor includes a display and a wireless device.
Figure 4A:
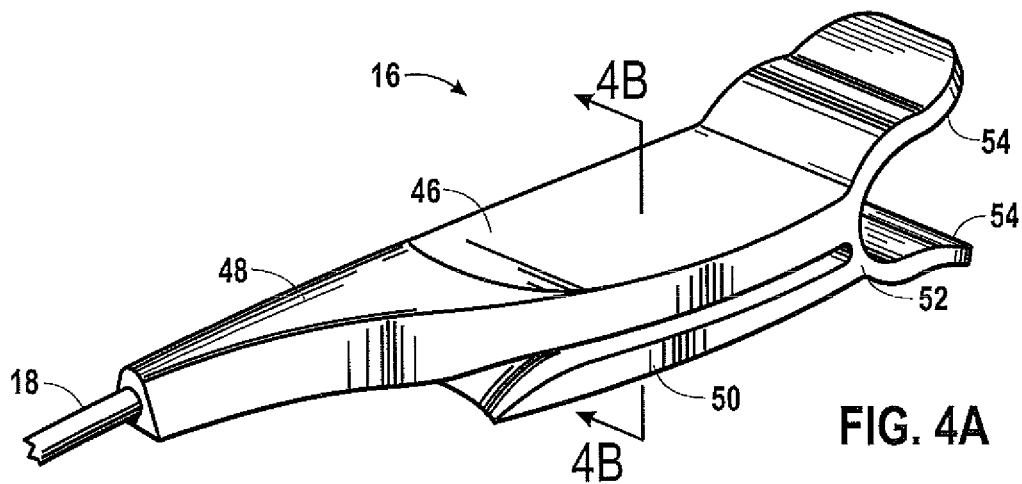
FIG. 4A is a perspective view of a flexible clip-style sensor, in accordance with an embodiment.
Figure 4B:
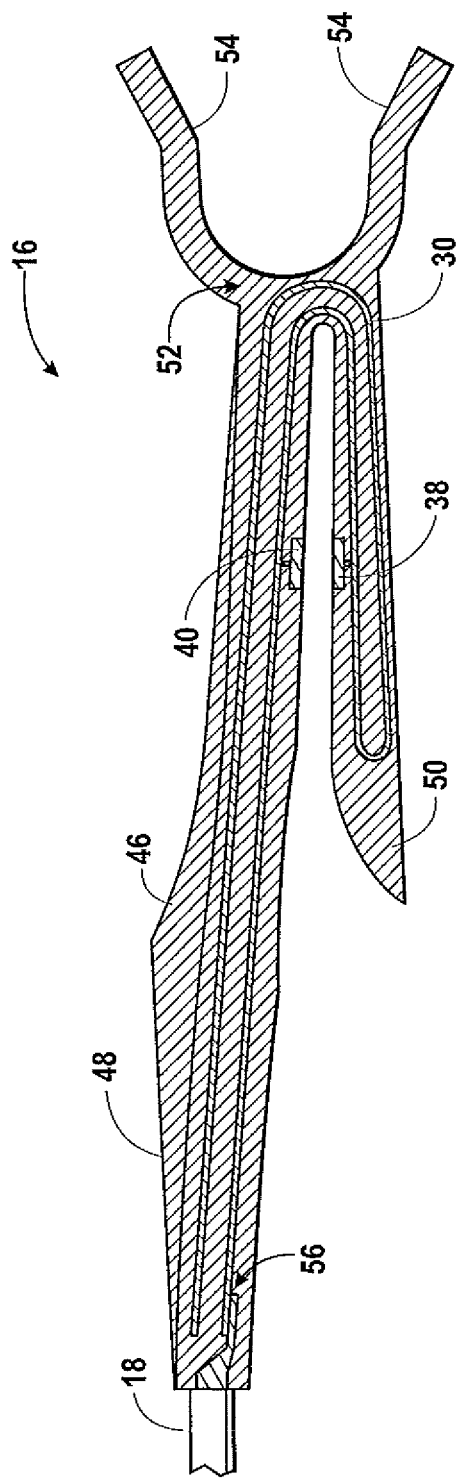
FIG. 4B is a cross-sectional view of the flexible clip-style sensor of FIG. 4A taken along line 4-4, in accordance with an embodiment.
Figure 5:
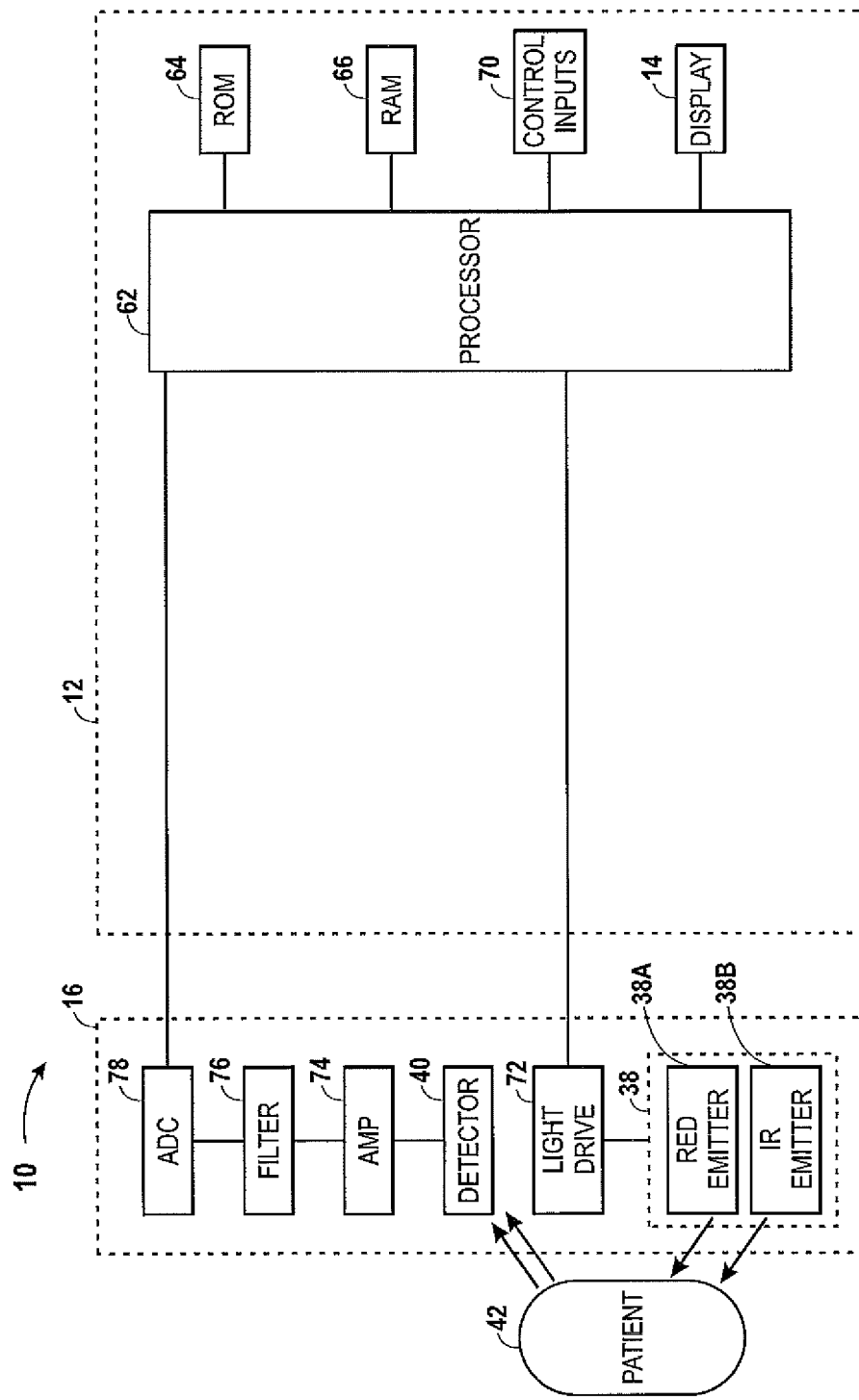
FIGS. 5-7 are block diagrams of the sensors of FIGS. 1-4 in accordance with various embodiments.
Figure 6:
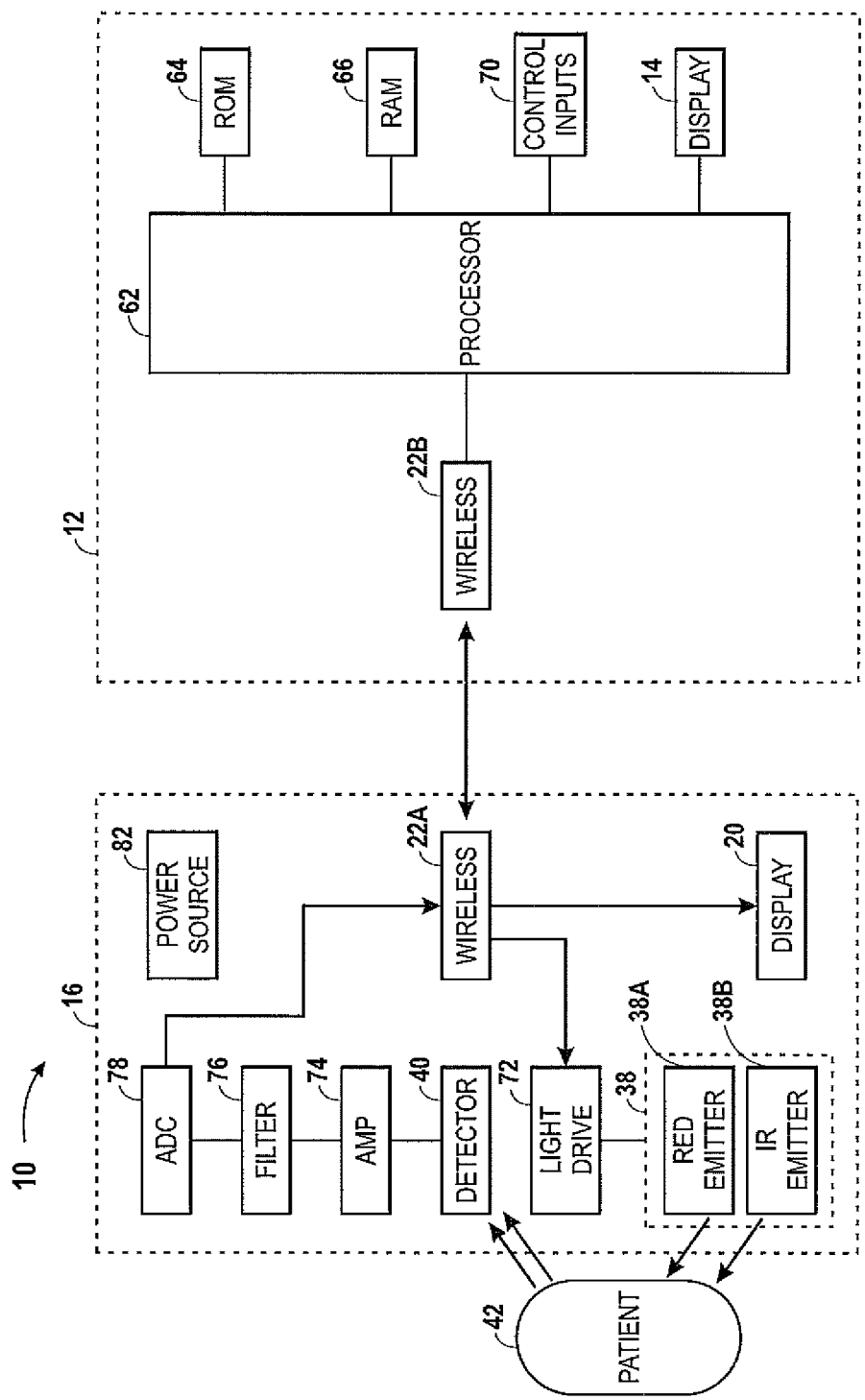
Figure 7:
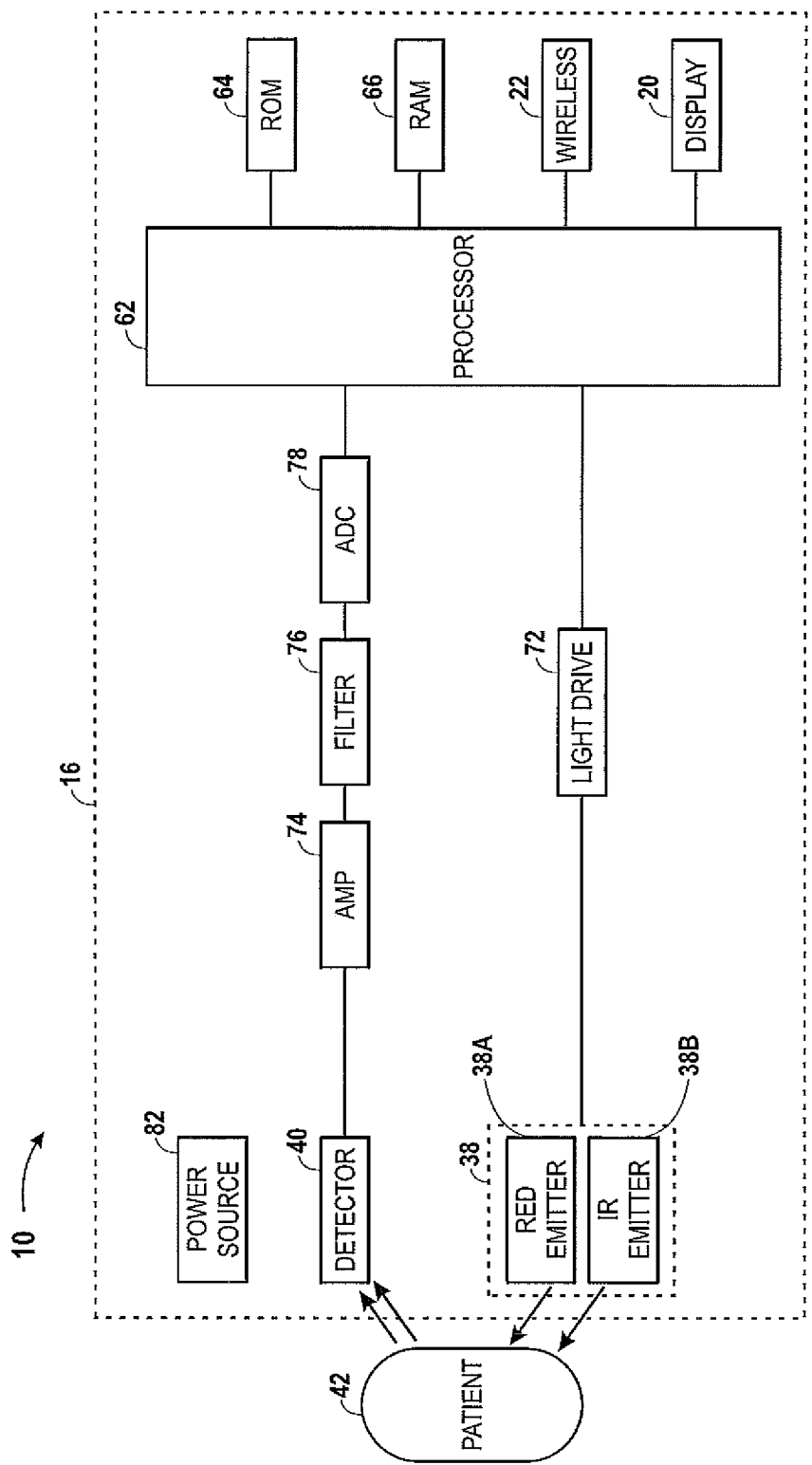

Additional details of the sensor 16 are provided with reference to FIGS. 2-7. Specifically, FIGS. 2-4 illustrate various embodiments of sensor construction, while FIGS. 5-7 illustrate the electrical components that may be included in various embodiments. Turning first to FIG. 2, a perspective view of the sensor 16 is illustrated. As shown in FIG. 2, the circuitry of the sensor 16 may be housed within a flexible outer covering that may include a flexible top layer 23 and a flexible bottom layer 24. Both the top layer 23 and bottom layer 24 may include flexible polymers, such as silicon polymers, polyvinylchloride, and polyethylene. The polymers may be elastomeric to provide for flexibility of the sensor 16 such that it may conform to the tissue of a patient. In some embodiments, the top and bottom layers 23 and 24 may include cloth or a bandage material, such as gauze. The top layer 23 and bottom layer 24 may be held together by an adhesive. For convenience, FIG. 2 shows the top layer 23 as partially separated from the bottom layer 24 to provide a view of the internal circuitry within the sensor 16. In some embodiments, the top layer 23 may include a window 26 to enable viewing of a display 20. The window 26 may be an unfilled aperture within the top layer 23 or, alternatively, the window may include a clear polymer layer. In some embodiments, the top layer 23 and bottom layer 24 may also include complimentary fastening mechanisms 28, such as rows of buttons or strips of hook and loop type fasteners, which allow the sensor 16 to be wrapped around an extremity of the patient and held in position.

As is also shown in FIG. 2, the sensor 16 may also include one or more flexible circuits 30 held between the top layer 23 and the bottom layer 24. The flexible circuits 30 provide the added functionality of the sensor 16, which will be described further below in relation to FIGS. 5-7. In embodiments with more than one flexible circuit 30, the flexible circuits 30 may be physically and communicatively coupled to one another by a flexible circuit board 32, such as a "flex" circuit board made from a flexible polymer substrate, such as polyimide. The flexible circuit board 32 may be communicatively coupled to electrical leads from the cable 18 at an electrical interface 34. In this way, signals from the monitor 12 may be routed to or from the emitter 38, detector 40, and other circuit components.

The flexible circuits 30 may include flexible semiconductors fabricated on a flexible polymer substrate according to any of several flexible semiconductor fabrication techniques. In some embodiments, for example, the flexible circuits 30 may include thin film transistors (TFTs), such as low-temperature polysilicon TFTs deposited on a flexible polymer substrate. In some embodiments, the TFTs may be deposited on the flexible polymer substrate by a method of chemical vapor deposition (CVD) or physical vapor deposition (PVD), such as sputtering. Furthermore, in some embodiments, the flexible circuits 30 may be inkjet printed on the polymer substrate at low temperature using a low-temperature liquid silicon, such as polysilane or cyclopentasilane.

The flexible circuits 30 may include some or all of the circuit components of the sensor 16, such as emitters, detectors, drivers, processors, batteries, etc, as will be described below. Among other things, the flexible circuits 30 may include the display 20 and the wireless device 22A. The display 20 may be any thin flexible display, such as a flexible organic light-emitting diode OLED display or a flexible electrophoretic display, for example. The wireless device 22A on the sensor 16 may include a flexible radio frequency antenna, such as a flexible microstrip antenna or flexible patch antenna, for example.

Sensors 16 in accordance with present embodiments may be either transmissive or reflective. In a transmissive sensor 16, emitted light signals pass completely through the patient's tissue before being received by the sensor 16. In a reflective sensor 16, the emitted light signals penetrate the patient's tissue only partially before being reflected back and received by the sensor 16. Embodiments of a transmissive sensor 16 and a reflective sensor 16 are illustrated in FIGS. 3A and 3B, respectively.

Figure 3A:
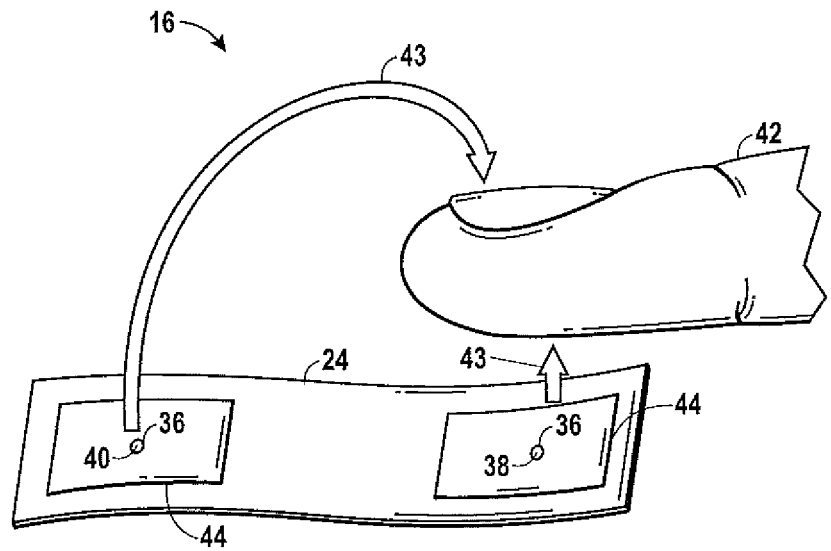
FIGS. 3A and 3B are perspective views of the back side of the bandage-style sensor of FIG. 2 in accordance with an embodiment.
Figure 3B:
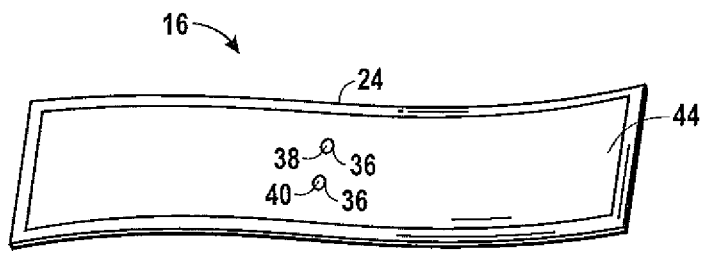

Turning first to FIG. 3A, a bottom layer 24 of a transmissive sensor 16 is illustrated in accordance with embodiments. The bottom layer 24 of the sensor 16 is held adjacent to the tissue of a patient so that the sensor 16 may detect physiological data of the patient through an emitter 38 and a detector 40, both of which may be held in close proximity to the skin or tissue of the patient. The emitter 38 may include a red emitter and an infra-red emitter that are configured to transmit electromagnetic radiation through the tissue of a patient. In accordance with this embodiment, the red and infra-red emitters may include light emitting diodes (LEDs) that emit electromagnetic radiation in the respective region of the electromagnetic spectrum. The radiation emitted by the emitter 38 into the patient's tissue is detected by the detector 40 after the radiation has passed through or reflected from blood perfused tissue of the patient 42, and the detector 40 generates an electrical signal correlative to the amount of radiation detected.

To facilitate the transmission of light through the patient's tissue, the bottom layer 24 of the sensor 16 may include transparent windows 36 that expose the emitter 38 and detector 40 and allow light to pass through the tissue of a patient from the emitter 38 to the detector 40. The windows 36 may be unfilled apertures within the bottom layer 24 or, alternatively, the windows 36 may include a clear polymer layer. The bottom layer 24 may also include one or more adhesive layers 44 for attaching the sensor 16 to the skin of the patient and securing the emitter 38 and the detector 40. Furthermore, the adhesive layers 44 may surround both the emitter 38 and the detector 40 to prevent the emitter 38 and the detector 40 from moving relative to the skin of the patient.

The emitter 38 may include any kind of light emitting diodes (LED) suitable for pulse oximetry, while the detector may include any suitable kind of photodiode. In some embodiments, the emitter 38 and the detector 40 may be flexible and may be formed directly on the flexible circuits 30 of the sensor 16. For example, the emitter 38 may include one or more organic light emitting diodes (OLEDs) formed on the plastic substrate of the flexible circuits 30. Additionally, the detector 40 may also include an organic diode configured to operate as a light-detecting photodiode. The emitter 38 and the detector 40 may be disposed on opposite sides of the tissue so that the detector 40 may detect light transmitted through the tissue by the emitter 38.

Turing now to FIG. 3B, a bottom layer 24 of a reflective sensor 16 is illustrated in accordance with embodiments. In this embodiment, as in FIG. 3A, the bottom layer 24 may also include one or more adhesive layers 44 that surround both the emitter 38 and the detector 40 and secure the emitter 38 and the detector 40 to the skin of the patient. In this embodiment, however, the sensor 16 may operate by reflecting light from the tissue of the patient, rather than transmitting light through the tissue. Accordingly, the emitter 38 and the detector 40 may be positioned close to one another to reduce the transmission path between the emitter 38 and the detector 40. In this embodiment, the sensor 16 may be disposed adjacent to any part of a patient's body that is conducive to measuring physiological parameters, such as the forehead, for example. Again, the flexibility of the flexible circuits 30 enables the sensor 16 to easily bend to fit the contour of the tissue to which it is attached.

Embodiments of the present invention may also include a clip-style sensor 16 configured to grasp the tissue of a patient. Turning to FIGS. 4A and 4B, an embodiment of a clip-style sensor 16 is illustrated, in accordance with embodiments. Turning first to FIG. 4A, the sensor 16 may include a sensor body 46 with an upper clip portion 48 and a lower clip portion 50 coupled together by a hinge 52 that allows the upper clip portion 48 and a lower clip portion 50 to flex outward to receive a body part of the patient, such as a patient's finger. As shown in FIG. 4A, the sensor body 46 may be a single, continuous structure that includes a semi-rigid polymer injection molded around the flexible circuitry 30 and other circuit components of the sensor 16. In this embodiment, the hinge 52 may be a living hinge formed by a thinning of the semi-rigid polymer; and the flexible circuits 30 may pass through the hinge 52. Further, the resiliency of the hinge 52 may provide a compressive force that holds the upper clip portion 48 and the lower clip portion 50 in place against the patient's tissue. In alternative embodiments, the upper clip portion 48 and the lower clip portion 50 of the sensor body 46 may be separate pieces coupled together by the hinge 52, which may be spring loaded to provide the compressive force for holding the upper clip portion 48 and the lower clip portion 50 against the patient's tissue.

Together, the upper clip portion 48 and the lower clip portion 50 may be configured to flex outward about the hinge 52 to allow the finger of a patient to be inserted into the sensor 16 for testing. Furthermore, the sensor body 46 may also include grips 54 to facilitate the flexing of the sensor body 48 and the placement of the sensor 16 around the patient's finger. As will be shown, both the upper clip portion 48 and the lower clip portion 50 may house a variety of flexible electronic circuits and devices for measuring biological parameters.

FIG. 4B shows a side cross-sectional view of the clip-style embodiment of sensor assembly 16. As shown in FIG. 4B, the sensor 16 includes a emitter 38 and a detector 40 embedded in the sensor 16 on opposite sides of the sensor 16. In this embodiment, light signals may be emitted by emitter 38 into the bottom of patient's finger, transmitted through the patient's finger tissue, and received by detector 40. The detector 38 and the emitter 40 may each include or be adjacent to a transparent window which allows light to be transmitted from the emitter 40 to the detector 38, through the patient's finger tissue.

As in the sensor 16 described in relation to FIGS. 1-3, the sensor 16 may include a flexible circuit 30. The flexible circuit 30 may include electrical leads located on a surface of the flexible circuit 30 at an electrical interface 56. The flexible circuit leads may be electrically coupled at the electrical interface 56 to electrical leads from the cable 18 so that signals may be routed to or from the emitter 38, detector 40, and other circuit components.

In other embodiments, the clip-style sensor 16 may also include a wireless device so that signals may be routed to or from the emitter 38, detector 40, and other circuit components wirelessly, and the cable 18 may not be present. In some embodiments, the flexible circuit 30 may be one continuous flexible circuit 30 that extends from the electrical interface 56 through both the upper clip portion 48 and the lower clip portion 50, bending approximately 180 degrees at the joint 30. Moreover, as shown in FIG. 4B, the flexible circuit 30 may be folded on itself one or more times to increase the amount of circuitry that may be included in the sensor 16. In some embodiments, the flexible circuit 30 may include a thin insulative sheet (not shown) to prevent electrical shorting between the folded layers. In other embodiments, electrical insulation may be provided by a thin insulative sheet imposed between the folded layers. By including the flexible circuit 30 in the clip-style sensor 16, a relatively large amount of circuitry may be included within the sensor 16, thus enhancing the capabilities of the sensor as described below while maintaining the flexibility, small size, and comfort of the sensor 16.

Various other physical embodiments of the sensor 16 with flexible circuitry 30 may be possible. In fact, many techniques may be used for holding the sensor 16 against the skin of a patient, and the examples recited above should not be considered an exhaustive list of possible embodiments.

Turning now to FIGS. 5-7, the electrical features of various embodiments of the sensor 16 are described. Embodiments of the sensor 16 may include various levels of additional functionality, some of which will be described below. For example, FIG. 5 describes a sensor 16 electrically coupled by a cable to a monitor 12, wherein the sensor 16 includes, among other things, circuitry for amplification, filtering, and digital conversion of the signals received by the detector 40. For another example, FIG. 6 describes a sensor 16 with circuitry that enables the sensor to communicate with the monitor 12 wirelessly. For yet another example, FIG. 7 describes a sensor 16 with a display 20 and circuitry for calculating and displaying some physiological parameters. It will be understood that an actual implementation described herein may include more or fewer components as needed for a specific application.

Turning first to FIG. 5, a block diagram of the monitoring device 10 with the sensor 16 is illustrated in accordance with an embodiment. As shown in FIG. 5, the monitor 12 may include one or more processors 62. The processor 62 may be configured to calculate physiological parameters using various algorithms programmed into the monitor 12 and based on signals received from the sensor 16. For example, the processor 62 may compute a percent oxygen saturation of hemoglobin and/or a pulse rate, among other useful physiological parameters.

The processor 62 may be connected to other component parts of the monitor 12, such as one or more read only memories (ROM) 64, one or more random access memories (RAM) 66, the display 20, and control inputs 70. The ROM 64 and the RAM 66 may be used in conjunction, or independently, to store the algorithms used by the processor 62 in computing physiological parameters. The ROM 64 and the RAM 66 may also be used in conjunction, or independently, to store signals received from the sensor 16 for use in the calculation of the aforementioned algorithms. The control inputs 70 may be provided to allow a user to interface with the monitor 12 and may include soft keys, dedicated function keys, a keyboard, and/or keypad type interfaces for providing parameters, data, and/or instructions to the monitor 12.

As described above in relation to FIGS. 3-4, the sensor 16 may include an emitter 38 and a detector 40. Additionally, the sensor 16 of FIG. 5 may also perform many of the functions traditionally performed by the monitor 12. For example, the sensor 16 may include a light drive 72 that provides signals to a red emitter 38A and an infra-red emitter 38B that cause the emitters 38A and 38B to produce the emitted light signals. The light drive 72 may be driven by an analog signal from the monitor 12, which controls the timing and intensity of the light signals emitted by the emitters 38A and 38B. The analog signal from the monitor 12 may then trigger the light drive 72 to generate an excitation signal that is transmitted to the emitters 38A and 38B. In accordance with an embodiment, the light drive 72 may be a simplified light drive circuit discussed in detail in U.S. patent application Ser. No. 12/343,799, entitled "LED Drive Circuit and Method for Using Same," by Ethan Peterson, which was filed Dec. 24, 2008, and is incorporated herein by reference in its entirety for all purposes. The simplified light drive 72 described therein may include fewer circuit components as compared to light drive circuits typically found on pulse oximetry monitors.

For another example of added sensor 16 functionality, the sensor 16 may also include circuitry for converting the analog signal received from the detector 40 into a digital signal. Specifically, the sensor 16 may include an amplifier 74 that amplifies the electrical signal generated by the detector 40 and a filter 76 that reduces unwanted signals located outside the frequencies of interest. The amplified and filtered signal may then be provided to an analog-to-digital converter (ADC) 78) that converts the analog signal into a digital format. The digital signal may then be provided to the monitor 12 for further processing, such as for the calculation of various physiological parameters. By transmitting a digital signal from the sensor 16 to the monitor 12 rather than an analog signal, the electrical interference introduced by the cable 18 may be reduced.

Turning now to FIG. 6, a block diagram of another embodiment of the monitoring device 12 with the sensor 16 is illustrated. As shown in FIG. 6, the sensor 16 may include the emitter 38 and the detector 40, as well the additional circuitry such as the light drive 72, the amplifier 74, the filter 76, and the ADC 78, as discussed above in relation to FIG. 5. In this embodiment, however, the sensor 16 and the monitor 12 both include wireless devices 22A and 22B that enable the sensor 16 and the monitor 12 to communicate wirelessly. In this way, the communications cable 18 may be eliminated. The wireless device 22A on the sensor 16 may also include driver circuitry (not shown) that receives the digital signal from the ADC 78 and generates an excitation signal for driving an antenna (not shown). In an embodiment, the sensor 16 may transmit data via a wireless communication protocol such as, but not limited to, WiFi, Bluetooth or ZigBee.

In some embodiments, the monitor 12 may communicate with several sensors 16 at the same time. In such embodiments, the operator of the monitor 12 may choose to view physiological data from one or more sensors 16 at any time. To correlate a sensor 16 with a particular patient 42, each sensor 16 may provide a unique identifier that allows the health care provider to match sensor 16 readings with the patient 42 wearing the sensor 16. In various embodiments, for example, each sensor 16 may be tuned to a slightly different broadcast frequency, or each sensor 16 may periodically broadcast an identification sequence.

As is also shown in FIG. 6, the sensor 16 may also include a display 20 that may display various information about the sensor 16 and/or the patient 42. In embodiments, the display 20 may include a numerical display. As such, the display 20 may receive incoming data and convert the data into a format suitable for driving the display 20. Furthermore, the display 20 may be configured to cycle through a set of display data, either on a timed basis or responsive to an input of the user.

In some embodiments, the display 20 may be configured to display data corresponding to the sensor 16, such as, for example, battery life and/or whether the sensor 16 is transmitting a wireless signal. Moreover, the display 20 may also be configured to display any useful data corresponding to a physiological parameter of a patient 42, such as, for example, a pulse rate and/or a blood-oxygen saturation level. In the embodiment shown in FIG. 6, the sensor 16 may not have processor circuitry suitable for generating the displayed physiological data. Therefore, the sensor 16 may receive physiological data through the wireless link provided by the wires devices 22A and 22B. As such, physiological data may be calculated by the processor 62 of the monitor 12 based on the digital signals received from the ADC 78 of the sensor 16, as discussed above. The physiological data may then be transmitted back to the sensor 16 via the wireless device 22B. The wireless device 22A may then route the physiological data to the display 20. The same physiological data may also be displayed on the display 14 of the monitor 12. Including a display 20 on the sensor 16 provides several advantages. For example, by displaying information regarding the battery life of the sensor 16, a caregiver may be alerted to replace or recharge the sensor 16. For another example, displaying information regarding the health of the patient in direct proximity to the patient, may enable the caregiver to devote greater attention to the patient while still monitoring physiological data provided by the sensor 16.

As is also shown in FIG. 6, the sensor 16 may include a power source 82, such as a battery for example. The power source 82 may serve to power several of the electrical components of the sensor 16 such as the light drive 72, the amplifier 74' the ADC 78, the wireless device 22A, and the display 20. The power source 82 may include any small, lightweight battery such as a "coin cell" or "button cell." In some embodiments, the power source 82 may include lithium ion batteries, such as nanowire batteries, i.e., high performance lithium ion batteries made from silicon nanowires. Furthermore, in some embodiments, the power source 82 may include one or more flexible thin-film batteries, which may be included in or coupled to the flexible circuitry 30. Furthermore, in some embodiments, the power source 82 may be rechargeable.

In some embodiments, the sensor 16 may be activated by coupling the power source 82 to the sensor circuitry 16. For example, an electrically insulative film (not shown) may be inserted between the power source 82 and an electrical contact coupling the power source 82 to the sensor circuitry, thus blocking the flow of current from the power source. In this way, removal of the electrically insulative film may activate the sensor 16.

Turning now to FIG. 7, a block diagram of another embodiment of a sensor 16 is illustrated. As discussed above, some or all of the circuit components shown in FIG. 7 may be included on one or more flexible circuits 30. As shown in FIG. 7, the sensor 16 may include several additional circuit components traditionally included in the monitor 12. For example, in addition to the signal processing and display capabilities discussed above, the sensor 16 may also include a processor 62. The processor 62 may be communicatively coupled to the light drive 72 for controlling the timing and intensity of the emitters 38A and 38B. Additionally, the processor 62 may be communicatively coupled to the ADC 78 for receiving the digital signal output of the ADC 78 and calculating physiological parameters based on the received digital signals. In some embodiments, the processor 62 may be a synchronous, i.e. clocked, circuit. In other embodiments, however, the processor 62 may be asynchronous, this reducing the power usage of the processor 62 and reducing the heat generated by the processor 62.

Other components of the sensor 16 may also be coupled to the processor 62, such as the display 20 and the wireless device 22. The display 20 may be a simplified display as discussed above in relation to FIG. 6. The wireless device 22A may allow the sensor 16 to transmit data wirelessly to a remote monitor 12. For example, the wireless device 22A may enable the sensor 16 to transmit digital signals received from the ADC 78 to the remote monitor, as discussed above in relation to FIG. 6. Additionally, the wireless device 22A may also enable the sensor 16 to transmit physiological parameters calculated by the sensor 16 to the remote monitor 12. The remote monitor 12 may use the data received from the sensor 16 to execute more advanced features that may not be included in the sensor 16. For example, the remote monitor 12 may calculate additional physiological data that may require more robust algorithms. For another example, the remote monitor 12 may store physiological data gathered over time by the sensor 16 in a long term memory. In this way, information pertaining to physiological trends over time may be stored and displayed by the monitor 12.

Furthermore, the processor(s) 62 may also be coupled to a memory such as read-only memory (ROM) 64 and/or a random access memory (RAM) 66. In certain embodiments, the ROM 64 may be used to store one or more pulse oximetry algorithms, which may be simplified pulse oximetry algorithms such that the computer code associated with those algorithms may be reduced and the circuit footprint of the ROM 64 on the flexible circuitry 30 may also be reduced. In other embodiments, the calculation algorithms may be hardwired into the processor 62, and the ROM 64 may be eliminated, thereby further reducing the circuit footprint of the sensor 16 circuitry on the flexible circuit 30. For example, the processor 62 may be an application specific integrated circuit (ASIC) or a programmable logic device (PLD). The RAM 66 may store intermediate values that are generated in the process of calculating patient parameters as well as certain software routines used in the operation of the sensor 16, such as measurement algorithms, light drive algorithms, and patient parameter calculation algorithms, for example.

From the embodiments describe above, it will be appreciated that several advantages may be achieved by including flexible circuitry within a medical sensor 16. The use flexible circuitry enables the addition of several electronic components that would traditionally be included in a monitor coupled to a sensor rather than the sensor itself. For example, the use of flexible semiconductor circuitry may enable the sensor to amplify and filter analog signals generated by the detector 40 and convert the analog signals into a digital signal that may then be transmitted to the monitor 12 with less electromagnetic interference and higher signal-to-noise ratio. Additionally, the use of flexible semiconductor circuitry may enable the sensor 16 to communicate wirelessly with the monitor 12, thus increasing the mobility and comfort of the patient. Furthermore, the use of flexible semiconductor circuitry may enable the sensor 16 to calculate and/or display physiological data detected by the sensor. Moreover, all of the benefits described above may be achieved while maintaining the comfort and flexibility of the sensor 16.

What is claimed is:

1. A sensor adapted for placement adjacent to tissue to be tested, comprising:
    at least one light emitter and at least one light detector capable of acquiring physiological data from a patient;
    a deformable integrated circuit comprising an analog-to-digital converter coupled to an output of the at least one light detector and configured to output a digital signal corresponding to the physiological data from the patient; and
    a flexible outer covering configured to be placed adjacent the tissue of a patient and to house the deformable integrated circuit and the emitter and the detector.

2. The sensor of claim 1, wherein the deformable integrated circuit comprises thin film transistors disposed on a flexible polymer substrate.

3. The sensor of claim 1, wherein the deformable integrated circuit comprises low-temperature polycrystalline silicon.

4. The sensor of claim 1, wherein the flexible outer covering is configured to be wrapped around a body part of a patient.

5. The sensor of claim 1, wherein the flexible outer covering comprises a clip configured to grasp an extremity of the patient.

6. The sensor of claim 1, wherein the at least one light emitter comprises at least one flexible, organic light emitting diode.

7. The sensor of claim 1, wherein the deformable integrated circuit comprises a wireless device coupled to an output of the analog-to-digital converter and configured to wirelessly transmit the digital signal to a monitor.

8. The sensor of claim 1, wherein the deformable integrated circuit comprises an amplifier coupled to an output of the at least one detector and a filter coupled to an output of the amplifier, wherein an output of the filter is coupled to an input of the analog-to-digital converter.

9. The sensor of claim 1, wherein the deformable integrated circuit comprises a drive circuit coupled to an input of the at least one emitter and configured to provide an electrical signal to the at least one emitter that causes the at least one emitter to emit at least one light signal into a tissue of the patient.

10. The sensor of claim 1, wherein the deformable integrated circuit comprises a display configured to display an output corresponding to the physiological data or to a state of the sensor.

11. The sensor of claim 1, wherein the deformable integrated circuit comprises a processor configured to receive the digital signal and generate an output corresponding to the physiological data.

12. A monitoring system, comprising:
- a sensor, comprising:
  - at least one light emitter and at least one light detector, capable of acquiring physiological data from a patient;
  - a deformable integrated circuit comprising an analog-to-digital converter coupled to an output of the at least one light detector and configured to output a digital signal corresponding to the physiological data from the patient; and
- a monitor configured to be communicatively coupled to the sensor and configured to receive the digital signal and generate an output corresponding to the physiological data.

13. The monitoring system of claim 12, wherein the output corresponding to the physiological data is transmitted from the monitor to the sensor; and wherein the sensor comprises a display configured to display the output.

14. The monitoring system of claim 12, wherein the deformable integrated circuit of the sensor comprises a flexible wireless transmitter configured to transmit the digital signal to the monitor.

15. The monitoring system of claim 12, wherein the deformable integrated circuit of the sensor comprises thin film transistors comprising low-temperature, polycrystalline silicon disposed on a flexible polymer substrate.

16. A method of generating physiological data, comprising:
- using a driving circuit disposed in a sensor to drive at least one light emitting diode disposed in the sensor and configured to emit a light signal into a tissue to be tested;
- receiving a modified light signal through a light detector disposed in the sensor, the modified light signal corresponding to the light signal after it has been transmitted through or reflected from the tissue to be tested;
- generating a digital signal through an analog-to-digital converter disposed in the sensor, the digital signal corresponding to the modified light signal; and
- generating a physiological parameter by processing the digital signal;
- wherein at least one of the driving circuit and the analog-to-digital converter comprises a deformable integrated circuit.

17. The method of claim 16, wherein generating a physiological parameter comprises sending the digital signal to a flexible processor disposed on the sensor.

18. The method of claim 16, comprising wirelessly transmitting the digital signal via a flexible wireless transmitter to a monitor, display, or other device.

19. The method of claim 18, comprising wirelessly transmitting the physiological parameter from the monitor, display, or other device to the sensor and displaying the physiological parameter on a flexible display disposed on an outer surface of the sensor.

20. The method of claim 16, wherein driving the light emitting diodes comprises sequentially activating a red light emitting diode and an infrared light emitting diode.

* * * * *